(12) United States Patent
Yarita

(10) Patent No.: US 7,171,262 B2
(45) Date of Patent: Jan. 30, 2007

(54) VITAL SIGN DISPLAY MONITOR

(75) Inventor: Masaru Yarita, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 724 days.

(21) Appl. No.: 10/352,073

(22) Filed: Jan. 28, 2003

(65) Prior Publication Data
US 2003/0144600 A1    Jul. 31, 2003

(30) Foreign Application Priority Data
Jan. 28, 2002  (JP) .......................... P2002-018597

(51) Int. Cl.
*A61B 5/04* (2006.01)
(52) U.S. Cl. ..................... 600/545; 600/544
(58) Field of Classification Search ................ 600/545
See application file for complete search history.

(56) References Cited

U.S. PATENT DOCUMENTS

| | | | |
|---|---|---|---|
| 5,299,118 A | | 3/1994 | Martens et al. |
| 5,792,069 A | * | 8/1998 | Greenwald et al. ......... 600/544 |
| 5,816,247 A | * | 10/1998 | Maynard .................... 600/544 |
| 6,224,549 B1 | * | 5/2001 | Drongelen .................. 600/300 |

FOREIGN PATENT DOCUMENTS

JP         2001-128952         5/2001

* cited by examiner

*Primary Examiner*—Charles A Marmor, II
*Assistant Examiner*—Patricia Mallari
(74) *Attorney, Agent, or Firm*—Sughrue Mion, PLLC

(57) ABSTRACT

At least an electroencephalogram (EEG) detected by a sensor is input from a signal input section as a vital sign signal. The vital sign signal is stored in a storage as vital sign data. A display includes a first display area, a second display area and a third display area. A controller reads out the vital sign data from the storage to display the vital sign signal on the display. The controller includes a first display processor, which displays the EEG in a real time manner, on the first display area, a second display processor, which displays the EEG at a time point in past, on the second display area, and a third display processor, which displays a time-varying trend of a parameter of the EEG, on the third display area. A designator designates a time point in past in the trend displayed in the third display area, so that the EEG at the designated time point is displayed on the second display area.

12 Claims, 5 Drawing Sheets

VITAL SIGN DISPLAY MONITOR

BACKGROUND OF THE INVENTION

The invention relates to a vital sign display monitor, and more particularly, to an electroencephalogram (EEG) display monitor.

A monitor, which synchronously displays in a time-varying manner vital signs, such as an electrocardiogram (ECG), a pulse wave, blood pressure, and an EEG, has hitherto been used in the medical science field and in clinical settings.

An electroencephalogram (EEG) is in particular one of important vital signs taken into consideration at the time of pronouncement of brain death at a clinical site, as in the case of ascertainment of a deep coma, loss of spontaneous respiration, pupil dilation, or electrocerebral inactivity (ECI). Also, EEG is important when diagnosing a deep coma, or judging effectiveness of anesthesia.

There has hitherto been unavailable a monitor which can compare the amplitude of an EEG waveform of the past with that of a current EEG waveform during the course of an EEG waveform showing active amplitudes shifting toward ECI. In order to compare the amplitudes of EEG waveforms with each other, the comparison is performed making reference to EEG waveforms printed on paper. For this reason, there are required intricate operations, such as an operation of selecting EEG waveforms to be compared from among a large quantity of measured EEG data.

When explaining to a family that a patient is in the state of brain death, a doctor explains the level of decrease in the amplitude of an EEG wave, which in turn leads to ECI, while showing a real-time EEG waveform appearing on a monitor or an EEG waveform printed on paper after brain death in conjunction with an EEG waveform printed on paper before brain death. This case is also attended with the same intricate operations as those mentioned previously; that is, complicated operations for selecting EEGs to be compared from among a large quantity of measured EEG measurement data. Moreover, intricate operations impose on a family an emotional difficulty against calmly accepting the brain death of a patient. Even if an anomaly is found in an EEG, intricate operations for comparing a normal EEG with an anomalous EEG are still required.

Also, it is intricate to select EEGs to be compared from among a large quantity of measured EEG data for diagnosing a deep coma, or judging effectiveness of anesthesia.

SUMMARY OF THE INVENTION

It is therefore an object of the invention to provide a vital sign display monitor capable of displaying in a comparative manner the change in EEG amplitude.

It is also an object of the invention to provide a vital sign display monitor capable of displaying in a comparative manner EEGs obtained at arbitrary time points.

In order to achieve the above objects, according to the invention, there is provided a vital sign display monitor, comprising:
  a signal input section, from which at least an electroencephalogram (EEG) detected by a sensor is input as a vital sign signal;
  a storage, in which the vital sign signal is stored as vital sign data;
  a display, including a first display area, a second display area and a third display area;
  a controller, which reads out the vital sign data from the storage to display the vital sign signal on the display, the controller including:
    a first display processor, which displays the EEG in a real time manner, on the first display area;
    a second display processor, which displays EEG at a time point in past, on the second display area; and
    a third display processor, which displays a time-varying trend of an amplitude of the EEG, on the third display area; and
  a designator, which designates a time point in past in the trend displayed in the third display area, so that the EEG at the designated time point is displayed on the second display area.

In such a configuration, the designator can designate a certain time point, presence or absence of an anomaly in an EEG, a time point when an anomaly arises in an EEG, a time point when an EEG shows an anomalous status, or a time point at which an EEG does not show any unique status. An EEG obtained at the specified time point can be compared, on the monitor screen, with the real time EEG displayed on the first display area.

According to the invention, there is also provided a vital sign display monitor, comprising:
  a signal input section, from which at least an electroencephalogram (EEG) detected by a sensor is input as a vital sign signal;
  a storage, in which the vital sign signal is stored as vital sign data;
  a display, including a first display area, a second display area and a third display area;
  a controller, which reads out the vital sign data from the storage to display the vital sign signal on the display, the controller including:
    a first display processor, which displays the EEG at a first time point, on the first display area;
    a second display processor, which displays the EEG at a second time point, on the second display area; and
    a third display processor, which displays a time-varying trend of an amplitude of the EEG, on the third display area; and
  a designator which designates at least one time point in past in the trend displayed in the third display area, so that the EEG at the designated time point is displayed on one of the first display area and the second display area.

In such a configuration, the designator can designate a certain time point, presence or absence of an anomaly in an EEG, a time point when an anomaly arises in an EEG, a time point when an EEG shows an anomalous status, or a time point at which an EEG does not show any unique status. EEGs obtained at the specified time points can be compared, on the monitor screen, with each other.

According to the invention, there is also provided a vital sign display monitor, comprising:
  a signal input section, from which at least an electroencephalogram (EEG) detected by a sensor is input as a vital sign signal;
  a storage, in which the vital sign signal is stored as vital sign data;
  a display, including a first display area and a second display area;
  a controller, which reads out the vital sign data from the storage to display the vital sign signal on the display, the controller including:
    a first display processor, which displays the EEG in a real time manner, on the first display area; and a second display processor, which displays the EEG at a time point in past, on the second display area; and a designator, which designates a certain time point in past, so that the EEG at the designated time point is displayed on the second display area.

In such a configuration, a certain time point, (e.g., before or after brain death) can be specified by the designator, thereby enabling comparison, on the monitor screen, between the EEG obtained at the specified time point and a real-time EEG displayed on the first display area.

According to the invention, there is also provided a vital sign display monitor, comprising:

a signal input section, from which at least an electroencephalogram (EEG) detected by a sensor is input as a vital sign signal;

a storage, in which the vital sign signal is stored as vital sign data;

a display, including a first display area, a second display area and a third display area;

a controller, which reads out the vital sign data from the storage to display the vital sign signal on the display, the controller including:

a first display processor, which displays the EEG at a first time point, on the first display area; and a second display processor, which displays the EEG at a second time point, on the second display area; and a designator which designates at least one certain time point in past, so that the EEG at the designated time point is displayed on one of the first display area and the second display area.

In such a configuration, a certain time point (e.g., before or after brain death) can be specified by the designator, thereby enabling comparison between the EEGs displayed on the first and second display areas.

According to the invention, there is also provided a vital sign display monitor, comprising:

a signal input section, from which at least an electroencephalogram (EEG) detected by a sensor is input as a vital sign signal;

a storage, in which the vital sign signal is stored as vital sign data;

a display, including a first display area, a second display area and a third display area;

a controller, which reads out the vital sign data from the storage to display the vital sign signal on the display, the controller including:

a first display processor, which displays the EEG in a real time manner, on the first display area;

a second display processor, which displays the EEG at a time point in past, on the second display area; and a third display processor, which displays a time-varying trend of a parameter of the EEG, on the third display area; and a designator, which designates a time point in past in the trend displayed in the third display area, so that the EEG at the designated time point is displayed on the second display area.

In such a configuration, the monitor enables comparison thereon between a designated EEG of the past displayed on the second display area and a real-time EEG displayed on the first display area.

According to the invention, there is also provided a vital sign display monitor, comprising:

a signal input section, from which at least an electroencephalogram (EEG) detected by a sensor is input as a vital sign signal;

a storage, in which the vital sign signal is stored as vital sign data;

a display, including a first display area, a second display area and a third display area;

a controller, which reads out the vital sign data from the storage to display the vital sign signal on the display, the controller including:

a first display processor, which displays the EEG at a first time point, on the first display area;

a second display processor, which displays the EEG at a second time point, on the second display area; and a third display processor, which displays a time-varying trend of a parameter of the EEG, on the third display area; and a designator which designates at least one time point in past in the trend displayed in the third display area, so that the EEG at the designated time point is displayed on at least one of the first display area and the second display area.

In such a configuration, an EEG obtained at an arbitrary time to be displayed on the first or second display area can be specified on the basis of the trend information of the EEG displayed on the third display area. The EEGs obtained at the specified time points can be compared with each other on the vital sign display monitor.

In the above configurations, it is preferable that the controller includes a filter which eliminates noise from the EEG to be displayed on at least one of the first display area and the second display area.

In such a configuration, noise can be eliminated from the EEG.

Here, it is preferable that the noise is stemmed from a cardiac potential.

In such a configuration, it is possible to eliminate noise stemming from a cardiac potential which is not essentially an EEG signal but may be erroneously determined to be the amplitude of the EEG.

In the configuration provided with the third display area, it is preferable that the controller includes a filter which eliminates noise from the trend to be displayed on the third display area.

In such a configuration, noise can be eliminated from also the trend displayed on the third display area.

Here, it is preferable that the noise is stemmed from a cardiac potential.

In such a configuration, it is possible to eliminate noise stemming from a cardiac potential which is not essentially an EEG signal but may be erroneously determined to be the amplitude of the EEG.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE PREFERRED EMBODIMENTS

An embodiment of a vital sign display monitor according to the invention will be described in detail hereinbelow making reference to the accompanying drawings.

Figure 1:
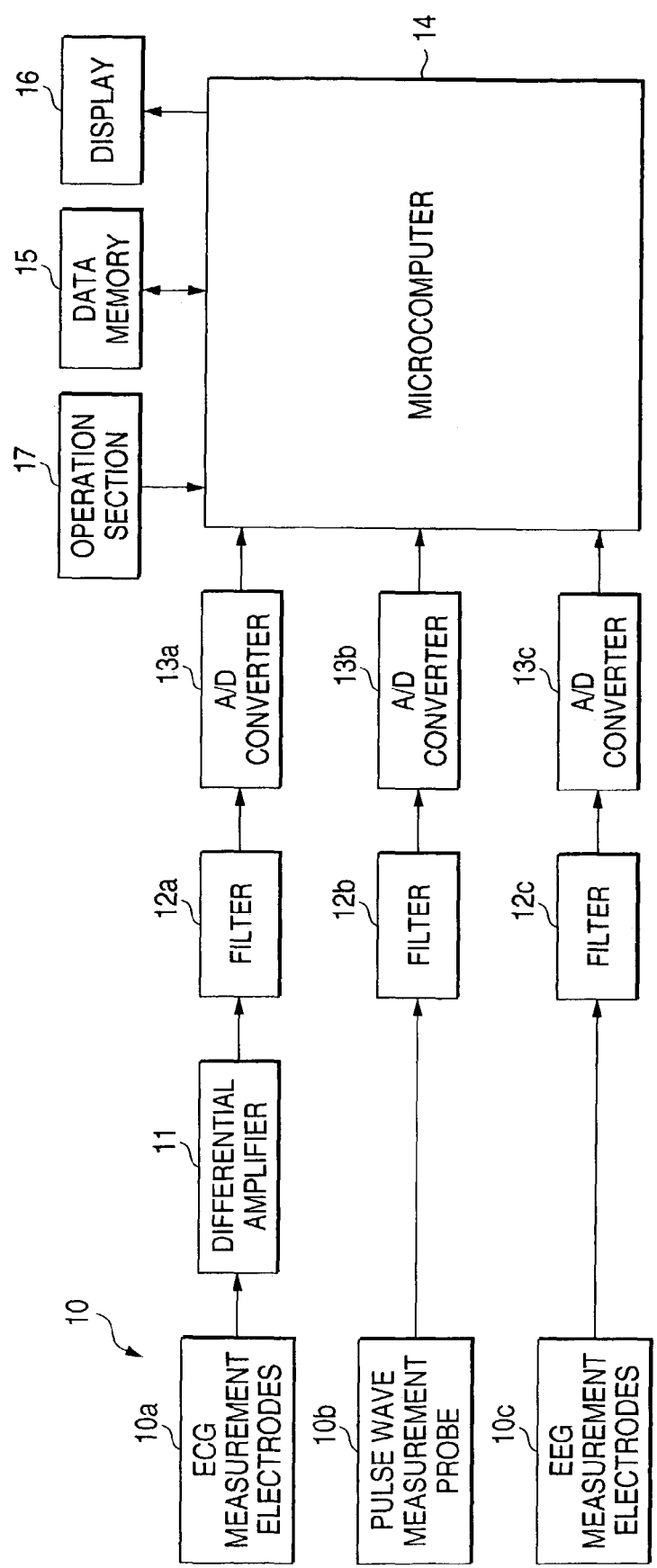
FIG. 1 is a schematic block diagram showing a vital sign display monitor according to an embodiment of the invention.

FIG. 1 is a schematic block diagram showing a vital sign display monitor according to an embodiment of the invention. As shown in FIG. 1, reference numeral 10 designates a vital sign signal detector constituted of sensors for sensing vital sign signals serving as vital signs, including an electrocardiogram (ECG) measurement electrodes 10a, a pulse wave measurement probe 10b, and an electroencephalogram (EEG) measurement electrodes 10c.

The ECG measurement electrodes 10a is connected to a microcomputer 14 serving as a controller via a differential amplifier 11, a filter 12a, and an A/D converter 13a. Further, the pulse wave measurement probe 10b is connected to the microcomputer 14 via a filter 12b and an A/D converter 13b. Moreover, the EEG measurement electrodes 10c is connected to the microcomputer 14 via a filter 12c and an A/D converter 13c.

The microcomputer 14 is provided with data memory 15 serving as a storage for storing vital sign signals relating to an EGC, a pulse wave, and an EEG along with time data pertaining to times when the vital sign signals are measured; a display 16 for displaying the vital sign signals in the form of waveforms; and an operation section 17 to be used for manipulating display modes of the vital sign signals.

A cardiac potential is detected by the ECG measurement electrodes 10a. The thus-detected cardiac potential is processed by the differential amplifier 11, the filter 12a, the A/D converter 13a, and the microcomputer 14. The thus-processed cardiac potential is stored in the data memory 15 and displayed in the form of a waveform on the display 16.

A pulse wave is detected by the pulse wave measurement probe 10b and is processed by the filter 12b, the A/D converter 13b, and the microcomputer 14. The thus-processed data are stored in the data memory 15 and displayed in the form of a waveform on the display 16.

An EEG is detected by the EEG measurement electrodes 10c and processed by the filter 12c, the A/D converter 13c, and the microcomputer 14. The thus-processed data is stored in the data memory 15 and displayed on the display 16 in the form of a waveform.

Figure 2:
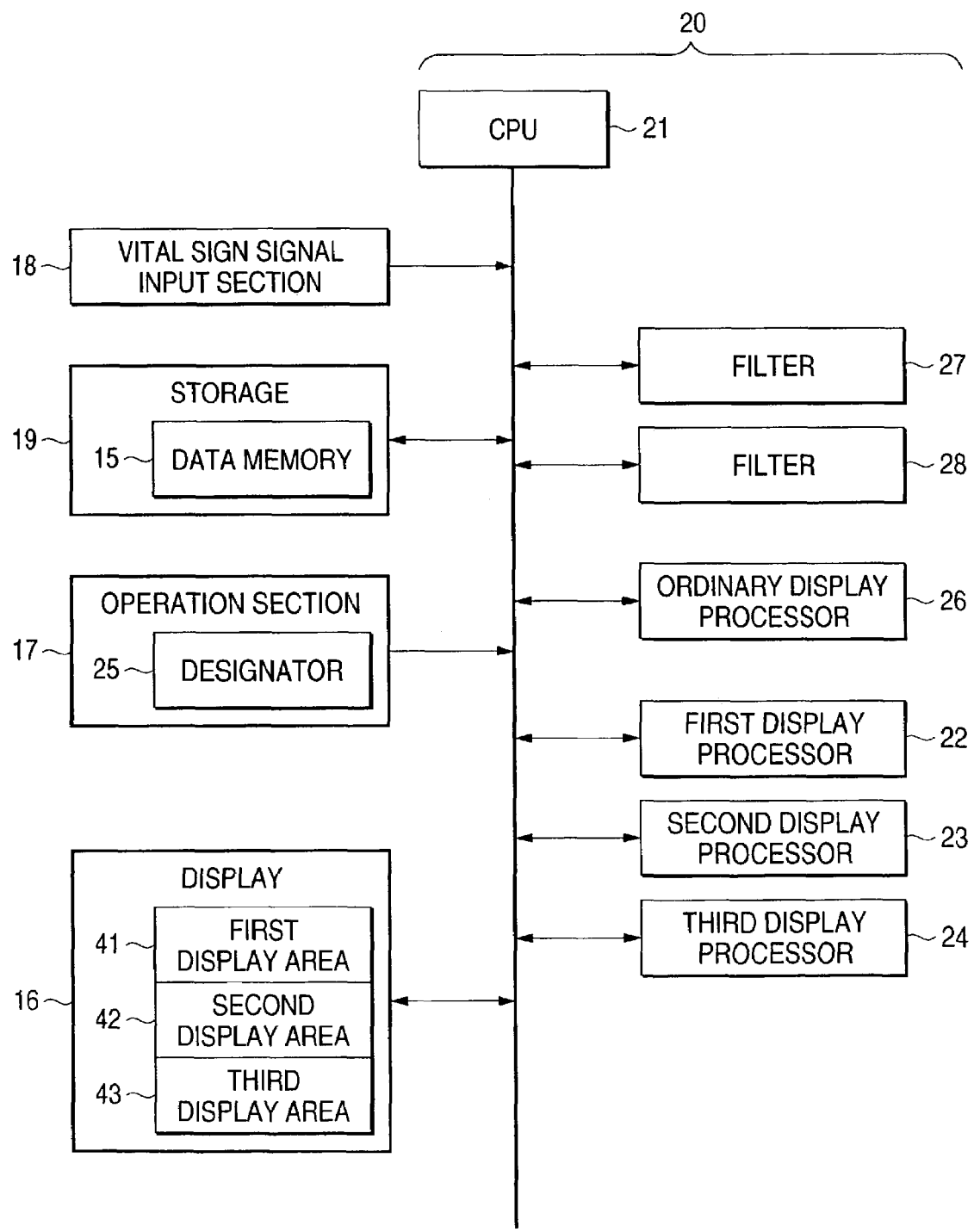
FIG. 2 is a descriptive view showing the system configuration of a controller provided in the vital sign display monitor.

FIG. 2 shows the system configuration of the vital sign display monitor of the embodiment. The vital sign display monitor is constituted of a vital sign signal input section 18 for inputting a vital sign signal serving as a vital sign, such as an EEG or the like; a storage 19 having the data memory 15 for storing, in the form of data, the vital sign signal input by the vital sign signal input section 18; a controller 20 for reading vital sign data stored in the storage 19 and displaying the vital sign data on the display 16 in the form of a waveform; and the operation section 17 for operating the controller 20.

The controller 20 is constituted by a microcomputer. Specifically, the controller 20 comprises a CPU 21; a first display processor 22 for displaying a real-time EEG on a first display area 41 of the display 16; a second display processor 23 for displaying an EEG of the past on a second display area 42 of the display 16; and a third display processor 24 for displaying a time-varying trend of amplitude of an EEG on a third display area 43 of the display 16.

The operation section 17 has a designator 25 for specifying a time point when the EEG of the past was measured, on the third display area 43 of the display 16. Processing is performed such that, on the basis of the designation operation performed by the designator 25, the EEG, which was measured in the past and is specified by the controller 20, is displayed on the second display area 42 of the display 16. The controller 20 is also provided with ordinary display processor 26 for displaying ordinary vital signs on the display 16.

Next, in relation to an example of control operation of the vital sign display monitor of the embodiment having the foregoing configuration, an example display of a monitor screen of the display 16 shown in FIGS. 3 and 4 and a control program shown in FIG. 5 will be described referring to FIG. 2.

As shown in FIG. 2, vital sign signals serving as vital signs to be measured and detected are input to the controller 20 by way of the vital sign signal input section 18 (step S1). In this case, the vital signs, which have been stored in a required storage medium beforehand, can be made so as to be input to the controller 20 by way of the vital sign signal input section 18. The vital sign signals input from the vital sign signal input section 18 are stored in the data memory 15 of the storage 19 (step S2).

Figure 3:
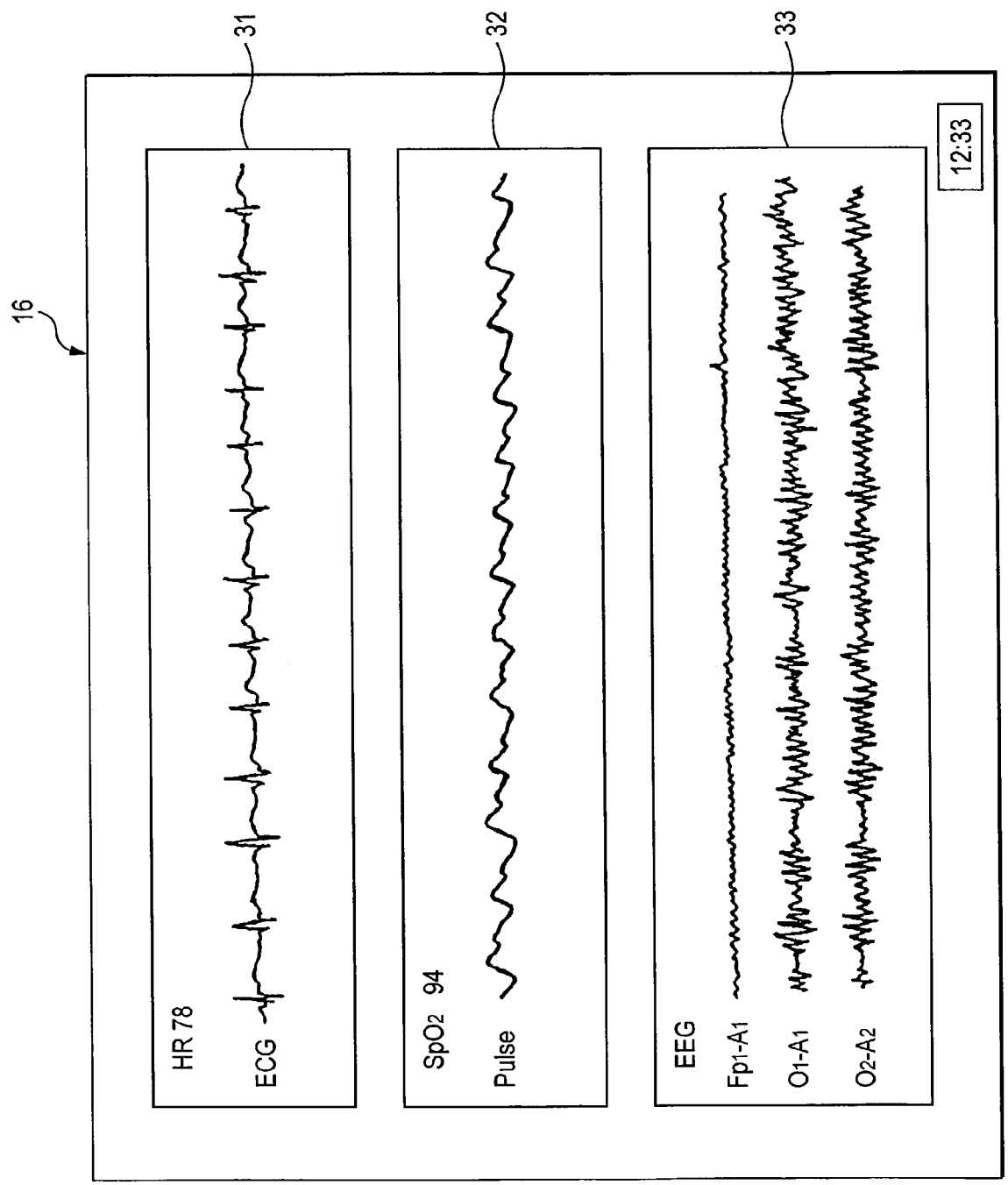
FIG. 3 is a descriptive view showing an illustrated example of a monitor screen of the vital sign display monitor in an ordinary state.

In this way, by the ordinary display processor 26, the vital signs stored in the data memory 15 are displayed on the monitor screen of the display 16 in such a manner as shown in, e.g., FIG. 3, thereby displaying waveforms of the vital signs (step S3). As shown in this figure, an ECG waveform on the display area 31 of the display 16, a pulse wave waveform on the display area 32, and an EEG waveform on the display area 33 are displayed in synchronism with each other and in a time-varying manner.

Figure 4:
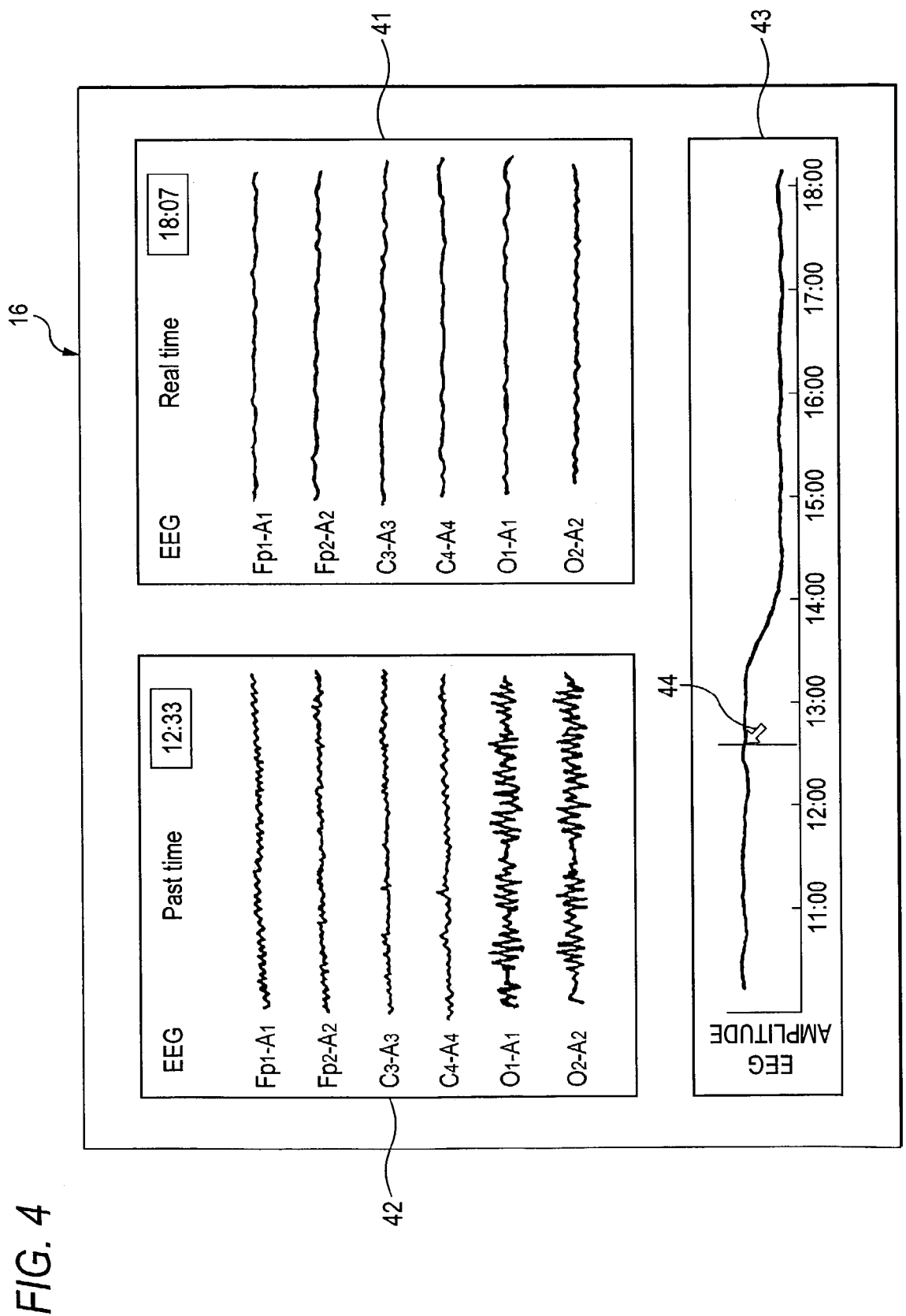
FIG. 4 is a descriptive view showing an illustrated example of a monitor screen of the vital sign display monitor when the waveform comparison is performed.
Figure 5:
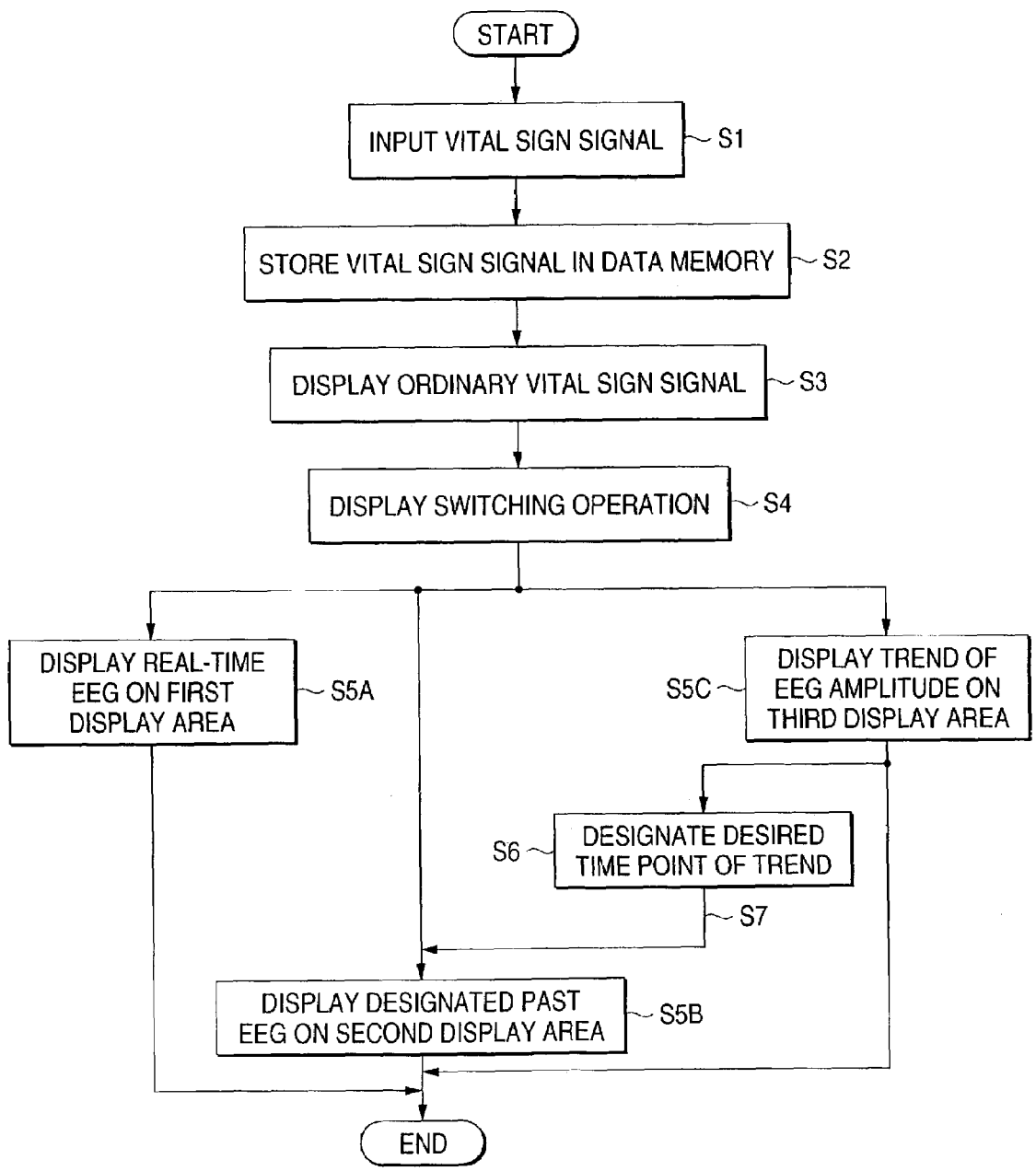
FIG. 5 is a flowchart showing an example of a control program for use with the vital sign display monitor.

Next, if switching of the displays on the display 16 is performed by the operation section 17 (step S4), the first display processor 22, the second display processor 23, and the third display processor 24 are activated, whereby monitor screens on the display 16 are switched to those shown in, e.g., FIG. 4. By activation of the first display processor 22, a real-time EEG is displayed on the first display area 41 of the display 16 in the form of a waveform (step S5A). By activation of the second display processor 23, an EEG of the past is displayed on the second display area 42 of the display 16 (step S5C). Moreover, by activation of the third display processor 24, a trend defined by a horizontal axis representing time and a vertical axis representing the amplitude of an EEG is displayed in the form of a waveform on the third display area 43 of the display 16 so that a distinction can be made between the EEG obtained before brain death and that obtained after brain death (step S5B).

In this case, brain death is represented as ECI. Hence, the amplitude of an EEG becomes extremely small at and after a time point when the patient has entered the state of brain death. Hence, the time point when the patient has entered brain death can be determined from the trend appearing on the third display area 43 of the display 16. In the example illustrated in FIG. 4, the patient is assumed to have entered brain death at a time of around 14:00.

A cursor 44 appearing on the monitor screen is moved by operation of the operation section 17; e.g., through use of a mouse, within the trend display of the EEG amplitude appearing on the third display area 43 of the display 16. While the cursor is superimposed on a desired position of a waveform, the mouse is clicked. Thus, by designating the position of the trend through use of the designator 25 (step S6), there is designated a time point when the EEG of the past to be displayed on the second display area 42 of the display 16 was measured. In response to designation of the time point when the EEG of the past was measured, EEG data pertaining to that time point are read from the data memory 15 by operation of the second display processor 23. The thus-read EEG data can be displayed on the second display area 42 of the display 16 (step S7). In the example illustrated in FIG. 4, an EEG measured at a time of 12:33 is displayed.

When the designator 25 does not designate a position on the trend of the EEG amplitude appearing on the third display area 43 of the display 16, the EEG of the past to be displayed on the second display area 42 of the display 16 can be set such that the EEG of the past obtained at the time point set in advance by the operation section 17 is displayed in the form of a waveform (step S5C). For example, if the time point to be set in advance is taken as a point immediately after commencement of measurement, variations appear in the amplitude of an EEG in a most noticeable manner. Hence, comparison between an EEG of the past and a current EEG is performed readily.

On the vital sign display monitor of the embodiment, an operator can specify a time point before the patient enters the state of brain death making reference to variations in amplitude of the EEG and can specify a time point at which the patient has become brain dead. The EEG to be displayed on the third display area 43 of the display 16 may be an EEG determined across specific electrodes or an average of EEGs determined across a plurality of electrodes. Alternatively, a running average may be displayed, or an envelope curve defined by peak values of the amplitude may be displayed.

As shown in FIG. 4, in the embodiment, an EEG measured in real time is set so as to be displayed on the first display area 41 of the display 16. However, for instance, an EEG determined at a time point specified by the third display area 43 may be set so as to be displayed on, e.g., the first display area 41. Specifically, the first and second display areas 41, 42 may be set so as to display EEGs obtained at the time points specified on the trend of the EEG amplitude appearing on the third display area 43.

Accordingly, in this case, the first display area 41 of the display 16 may be designated by the operation section 17, and the designator 25 specifies a position at which an EEG is to be displayed, on the trend of the EEG amplitude appearing on the third display area 43 of the display 16. As a result, the EEG which was measured at the designated time and stored in the data memory 15 is read by the first display processor 22. The EEG measured at the designated time point can be displayed on the first display area 41 of the display 16. In this way, EEGs which were measured at arbitrary designated time points and stored in the data memory 15 are individually displayed on the first and second display areas 41, 42 of the display 16 respectively, thus facilitating comparison between the EEGs.

In the embodiment, two display areas; that is, the first display area 41 and the second display area 42, are provided on the display 16 as display areas to be used for displaying EEGs. However, three or more display areas can be provided. In this case, EEGs measured at the time points designated in the third display area 43 may be set so as to be displayed on the respective display areas. Alternatively, any one of the three or more display areas to be used for displaying EEGs may be set so as to display a real-time EEG at all times.

In the embodiment, the first and second display areas 41, 42 are arranged side by side on the display 16. However, they may be provided in a vertical column. Alternatively, a new window screen can be made so as to be popped up, thereby displaying the second display area 42 or a new display area.

An ECG and other vital signs can be provided so as to be displayed synchronously on the display areas where an EEG is displayed in real time.

Further, the third display area 43 of the display 16 can be set so as to display the trend of an EEG parameter indicating an EEG other than the amplitude of an EEG. Alternatively, the third display area 43 may be set so as to be able to display EEG parameters which can serve as indices for suggesting an anomaly in an EEG.

In the above embodiment, the monitor is applied for monitoring brain-death patient. Alternatively, the monitor can be applied for monitoring a deep coma, or judging effectiveness of anesthesia.

As shown in FIG. 2, the vital sign display monitor of the invention can be provided with a filter 27 for eliminating noise stemming from a cardiac potential during measurement of an EEG. In this case, when an EEG signal input by way of the vital sign signal input section 18 is stored in the data memory 15 of the storage 19, the EEG signal is stored in the data memory 15 after having been filtered by the filter 27. As a result, noise stemming from the cardiac potential can be appropriately eliminated from the EEG appearing on the first display area 41 and from that appearing on the second display area 42, both areas belonging to the display 16 shown in FIG. 4.

In relation to a trend to be displayed on the third display area 43 of the display 16 shown in FIG. 4, an EEG parameter, such as the amplitude of an EEG may be displayed as a trend as a result of processing an EEG from which the noise stemming from a cardiac potential has been eliminated.

The reason why such a filter 27 is useful is that noise stemming from a cardiac potential is not essentially an EEG signal but may be erroneously recognized to be the amplitude of the EEG. Further, if noise stemming from a cardiac potential is superimposed on an EEG, the family of the patient desire to believe the noise to be the amplitude of an EEG, which in turn poses emotional difficulty for the family accepting the brain death of the patient.

The filter of this type is not limited to the filter 27 to be used for eliminating noise stemming from a cardiac potential. For instance, a filter 28 to be used for reducing noise, such as a filter which performs averaging operation, may be provided in lieu of the filter 27. Even in this case, the same usefulness as that yielded previously can be attained.

What is claimed is:

1. A vital sign display monitor, comprising:
    a signal input section, from which at least an electroencephalogram (EEG) detected by a sensor is input as a vital sign signal;
    a storage, in which the vital sign signal is stored as vital sign data;
    a display, simultaneously displaying a first display area, a second display area and a third display area;
    a controller, which reads out the vital sign data from the storage to display the vital sign signal on the display, the controller including:
    a first display processor, which displays the EEG in a real time manner, on the first display area;
    a second display processor, which displays the EEG at a time point in the past, on the second display area; and
    a third display processor, which displays a time-varying trend of a parameter of the EEG, on the third display area; and a designator, which designates a time point in the past in the trend displayed in the third display area, so that the EEG at the designated time point is displayed on the second display area.

2. The vital sign display monitor as set forth in claim 1, wherein the controller includes a filter which eliminates noise from the electroencephalogram to be displayed on at least one of the first display area and the second display area.

3. The vital sign display monitor as set forth in claim 1, wherein the controller includes a filter which eliminates noise from the trend to be displayed on the third display area.

4. The vital sign display monitor as set forth in claim 3, wherein the noise is stemmed from a cardiac potential.

5. A vital sign display monitor, comprising:
- a signal input section, from which at least an electroencephalogram (EEG) detected by a sensor is input as a vital sign signal;
- a storage, in which the vital sign signal is stored as vital sign data;
- a display, simultaneously displaying a first display area, a second display area and a third display area;
- a controller, which reads out the vital sign data from the storage to display the vital sign signal on the display, the controller including:
- a first display processor, which displays the EEG in a real time manner, on the first display area;
- a second display processor, which displays the EEG at a time point in the past, on the second display area; and
- a third display processor, which displays a time-varying trend of an amplitude of the EEG, on the third display area; and
- a designator, which designates a time point in the past in the trend displayed in the third display area, so that the EEG at the designated time point is displayed on the second display area.

6. The vital sign display monitor as set forth in claim 5, wherein the controller includes a filter which eliminates noise from the trend to be displayed on the third display area.

7. The vital sign display monitor as set forth in claim 5, wherein the controller includes a filter which eliminates noise from the electroencephalogram to be displayed on at least one of the first display area and the second display area.

8. The vital sign display monitor as set forth in claim 7, wherein the noise is stemmed from a cardiac potential.

9. The vital sign display monitor as set forth in claim 6, wherein the noise is stemmed from a cardiac potential.

10. A vital sign display monitor, comprising:
- a signal input section, from which at least an electroencephalogram (EEG) detected by a sensor is input as a vital sign signal;
- a storage, in which the vital sign signal is stored as vital sign data; a display, simultaneously displaying a first display area and a second display area;
- a controller, which reads out the vital sign data from the storage to display the vital sign signal on the display, the controller including:
- a first display processor, which displays the EEG in a real time manner, on the first display area; and
- a second display processor, which displays the EEG at a time point in the past, on the second display area; and
- a designator, which designates a certain time point in the past, so that the EEG at the designated time point is displayed on the second display area,
- wherein the first display area displays the EEG having a length corresponding to a first time period, and the second display area displays the EEG in the past having a length corresponding to the first time period.

11. The vital sign display monitor as set forth in claim 10, wherein the controller includes a filter which eliminates noise from the electroencephalogram to be displayed on at least one of the first display area and the second display area.

12. The vital sign display monitor as set forth in claim 11, wherein the noise is stemmed from a cardiac potential.

* * * * *